US010695212B2

(12) United States Patent
Lambert (10) Patent No.: US 10,695,212 B2
(45) Date of Patent: Jun. 30, 2020

(54) HAND COVER

(71) Applicant: Garry W. Lambert, The Woodlands, TX (US)

(72) Inventor: Garry W. Lambert, The Woodlands, TX (US)

( * ) Notice: Subject to any disclaimer, the term of this patent is extended or adjusted under 35 U.S.C. 154(b) by 347 days.

(21) Appl. No.: 15/243,368

(22) Filed: Aug. 22, 2016

(65) Prior Publication Data

US 2017/0049603 A1    Feb. 23, 2017

Related U.S. Application Data

(60) Provisional application No. 62/208,421, filed on Aug. 21, 2015.

(51) Int. Cl.
*A61F 5/37* (2006.01)
*A61F 5/058* (2006.01)
*A61M 5/52* (2006.01)

(52) U.S. Cl.
CPC ............ *A61F 5/37* (2013.01); *A61F 5/05866* (2013.01); *A61F 5/3723* (2013.01); *A61M 5/52* (2013.01)

(58) Field of Classification Search
CPC ....... A61F 5/37; A61F 5/3726; A61F 5/05866
USPC ...................... 128/877–879; 602/3
See application file for complete search history.

(56) References Cited

U.S. PATENT DOCUMENTS

| 1,537,811 | A | 5/1925 | Epling |
| 2,695,999 | A | 12/1954 | Arnold |
| 3,403,408 | A | 10/1968 | Helfer |
| 3,415,244 | A * | 12/1968 | Block ................ A61F 5/37 |
| | | | 128/879 |
| 3,741,207 | A | 6/1973 | Fuson |
| 4,887,616 | A | 12/1989 | Baijnath |
| 5,312,385 | A * | 5/1994 | Greco ............... A61H 35/00 |
| | | | 128/DIG. 24 |
| 5,349,966 | A | 9/1994 | Garcia |
| 5,551,086 | A | 9/1996 | Albanese |
| 5,605,534 | A * | 2/1997 | Hutchison ......... A61F 13/041 |
| | | | 128/849 |
| 5,845,643 | A * | 12/1998 | Vergano ........... A61F 5/05866 |
| | | | 128/877 |
| 6,283,126 | B1 | 9/2001 | Jessen |
| 6,482,168 | B1 | 11/2002 | Betcher |
| 6,895,971 | B1 * | 5/2005 | Evans ............... A61F 15/004 |
| | | | 128/869 |
| D608,953 | S | 1/2010 | Foster et al. |
| 2003/0200593 | A1 | 10/2003 | Chou |
| 2006/0010553 | A1 | 1/2006 | Villarreal |

(Continued)

FOREIGN PATENT DOCUMENTS

EP          0966892 A2    12/1999
WO     2009/079556 A2     6/2009

*Primary Examiner* — Keri J Nelson
(74) *Attorney, Agent, or Firm* — Dorsey & Whitney LLP (57) ABSTRACT

A hand cover includes a protective housing secured to an adjustment mechanism. The protective housing inhibits contact between the hand and the external environment. The adjustment mechanism secures the hand cover to the user. An optional upper access aperture provides air circulation and access to the hand. An optional lateral access aperture also provides access to the hand. An optional positioning mechanism helps maintain the hand cover in place. Attachment anchors for restraints or exercise bands may be provided and devices for orienting and securing IV lines may be provided.

20 Claims, 5 Drawing Sheets

(56) References Cited

U.S. PATENT DOCUMENTS

2006/0116621 A1 6/2006 Barker
2011/0289642 A1 12/2011 Pena
2012/0192877 A1 8/2012 Chaves

* cited by examiner

HAND COVER

CROSS REFERENCE TO RELATED APPLICATION

The present application claims priority to U.S. Provisional Patent Application No. 62/208,421 filed 21 Aug. 2015 entitled "Hand Cover," which is hereby incorporated herein by reference in its entirety.

TECHNICAL FIELD

The technology described herein relates to hand covers and methods of using the same.

BACKGROUND

Critical care hospital patients often receive medically necessary interventions such as endotracheal tubes, intravenous (IV) lines, nasogastric tubes, and urinary catheters. Medically unsupervised removal of a device, such as the intentional or unintentional removal of a tube or line by a patient, can cause life-threatening situations. The standard of care includes tying cloth restraints around a patient's wrists and securing the restraints to the patient's bed frame with cloth strands short enough to prevent the patient's hands from reaching and moving or removing the devices. The standard of care also includes sedating the patient.

Restraint can be physically uncomfortable for the patient and emotionally disturbing to the patient's family and friends. Restraint also increases the risk of critical illness polyneuropathy (CIP), also known as critical care weakness (CCW). Up to 30% of critical care patients develop CIP, which is characterized by profound muscle weakness and neurological dysfunction. CIP can extend a patient's hospital stay for days or even weeks and worsen a patient's prognosis for improvement.

Pediatric, cognitively impaired, and other non-critical patients may intentionally or unintentionally move or remove medical interventions such as wound dressings, IV lines, and nasogastric tubes.

Critical care patients may benefit from muscle strengthening exercise to improve muscle tone or strength or help prevent muscle atrophy. Some patients have arterial IV lines in or near the wrist and may benefit from maintaining the wrist in a cocked position and securing the lines out of the way of the hand.

The information included in this Background section of the specification, including any references cited herein and any description or discussion thereof, is included for technical reference purposes only and is not to be regarded as subject matter by which the scope of the invention as defined in the claims is to be limited.

SUMMARY

The technology disclosed herein relates to hand covers. The hand covers may be used to inhibit a user from moving or removing medical interventions such as endotracheal tubes, intravenous (IV) lines, nasogastric tubes, urinary catheters, and wound dressings. The hand cover includes a protective housing secured to an adjustment mechanism. The protective housing surrounds a hand and inhibits contact between the hand and the external environment. The protective housing resists deformation and may be constructed of a stiff plastic. The adjustment mechanism is adjustable and secures the hand cover to the hand of the user.

In some embodiments, the protective housing is ribbed to provide extra support or stiffness. In some embodiments, the protective housing is fenestrated to provide air circulation to the hand.

In some embodiments, the protective housing has an upper access aperture to provide air circulation and access to the hand. The upper access aperture may also reduce a user's sense of restriction, restraint, or claustrophobia. The upper access aperture may be releasably openable or closable.

In some embodiments, the protective housing has a lateral access aperture to provide access to the hand without removing the hand cover. The lateral access aperture may be releasably closable.

In some embodiments, the protective housing has a positioning mechanism to inhibit a user from moving or removing medical interventions as well as to maintain the hand cover in place.

In some embodiments, the adjustment mechanism is provided with an attachment point for securing restraints that help restrain upper extremity movement of the user or for securing exercise bands to enable a user to perform therapeutic exercises.

In some embodiments, the adjustment mechanism is provided with at least one retention device for positioning and securing tubes or lines away from the user's hand.

In some embodiments, the hand cover is provided with a splint and cocking mechanism for maintaining the hand or wrist in a cocked position. The splint includes a hand portion and a wrist portion. In some embodiments, the splint is provided with a securing member that encircles the forearm and helps maintain the splint in place.

In one implementation, a method for using the hand cover, such as to inhibit a user from moving or removing a medical intervention, is provided. The hand cover is applied over a user's hand. The size of the adjustment mechanism is adjusted to fit the wrist of the user and is secured at its adjusted size. The protective housing surrounds the hand and thereby inhibits contact between the hand and the external environment.

In another implementation, a method for using the hand cover including an upper access aperture, such as to provide access and air circulation to the hand, is provided. The protective housing and adjustment mechanism are used according to the method described above. The upper access aperture may be fixed in an open position or may be closable.

In another implementation, a method for using the hand cover including a lateral access aperture, such as to provide access to the hand, is provided. The protective housing and adjustment mechanism are used according to any method described above. The lateral access aperture may be opened or closed to permit or inhibit, respectively, access to the hand.

In another implementation, a method for using the hand cover including a positioning mechanism, such as to inhibit the hand cover from moving in relation to the hand, is provided. The protective housing is guided onto the hand such that the base of the thumb is captured by the positioning mechanism. The adjustment mechanism is used according to any method described above.

In another implementation, a method for using the hand cover including an attachment point, such as to attach restraints, cords, or bands, is provided. The protective housing and adjustment mechanism are used according to any method described above. Restraints may be attached to help restrain upper extremity movement of the user. Cords or exercise bands may be attached such that the user can perform strengthening exercises while in a hospital bed.

In another implementation, a method for using the hand cover including a retention device, such as to selectively position and secure IV lines, is provided. The protective housing and adjustment mechanism are used according to any method described above. The IV lines are positioned and secured away from the user's hand.

In another implementation, a method for using the hand cover including a splint and cocking mechanism, such as to maintain the hand or wrist in the cocked position, is provided. The protective housing and adjustment mechanism are used according to any method described above. The splint, which may be integral with the protective housing, is positioned behind the hand and wrist. The hand is captured by the cocking mechanism and is thereby secured in the cocked position.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

A hand cover is disclosed herein. As an introduction, the hand cover may be generally understood as including a protective housing secured to a user by an adjustment mechanism. The protective housing permits full arm, wrist, and hand movement while also inhibiting a user's manipulation or removal of a medical device applied to the user. The adjustment mechanism maintains the protective housing in place relative to the hand, and also aids in applying and removing the hand cover with minimal disruption to the user. In some implementations, an opening is formed at an end portion of the protective housing, which provides air circulation and access to the top portion of the hand. It may help reduce a user's sense of restriction, restraint, or claustrophobia. In some implementations, a lateral opening is formed in the protective housing to provide access to the lower portion of the hand while the hand cover is in use. In some implementations, a positioning mechanism helps maintain the hand cover in place while the hand cover is in use. In some implementations, the adjustment mechanism includes an attachment point to which restraints or exercise bands can be attached. In some implementations, the adjustment mechanism includes a device for securing IV lines away from the user's hand. In some implementations, a splint helps maintain the hand or wrist in a cocked position.

Figure 1:
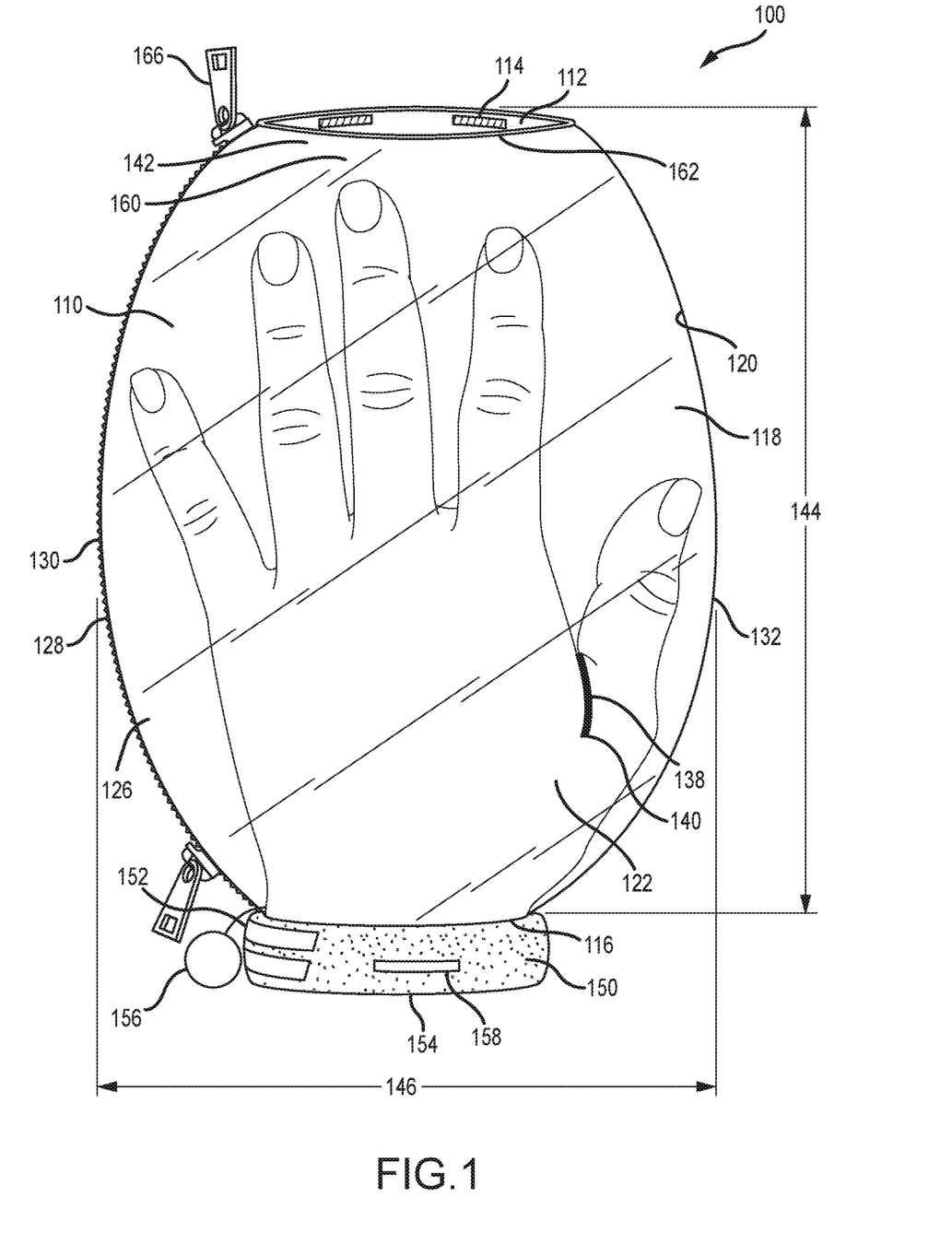
FIG. 1 is a front schematic view of a hand cover according to one embodiment applied to a patient's hand.
Figure 2:
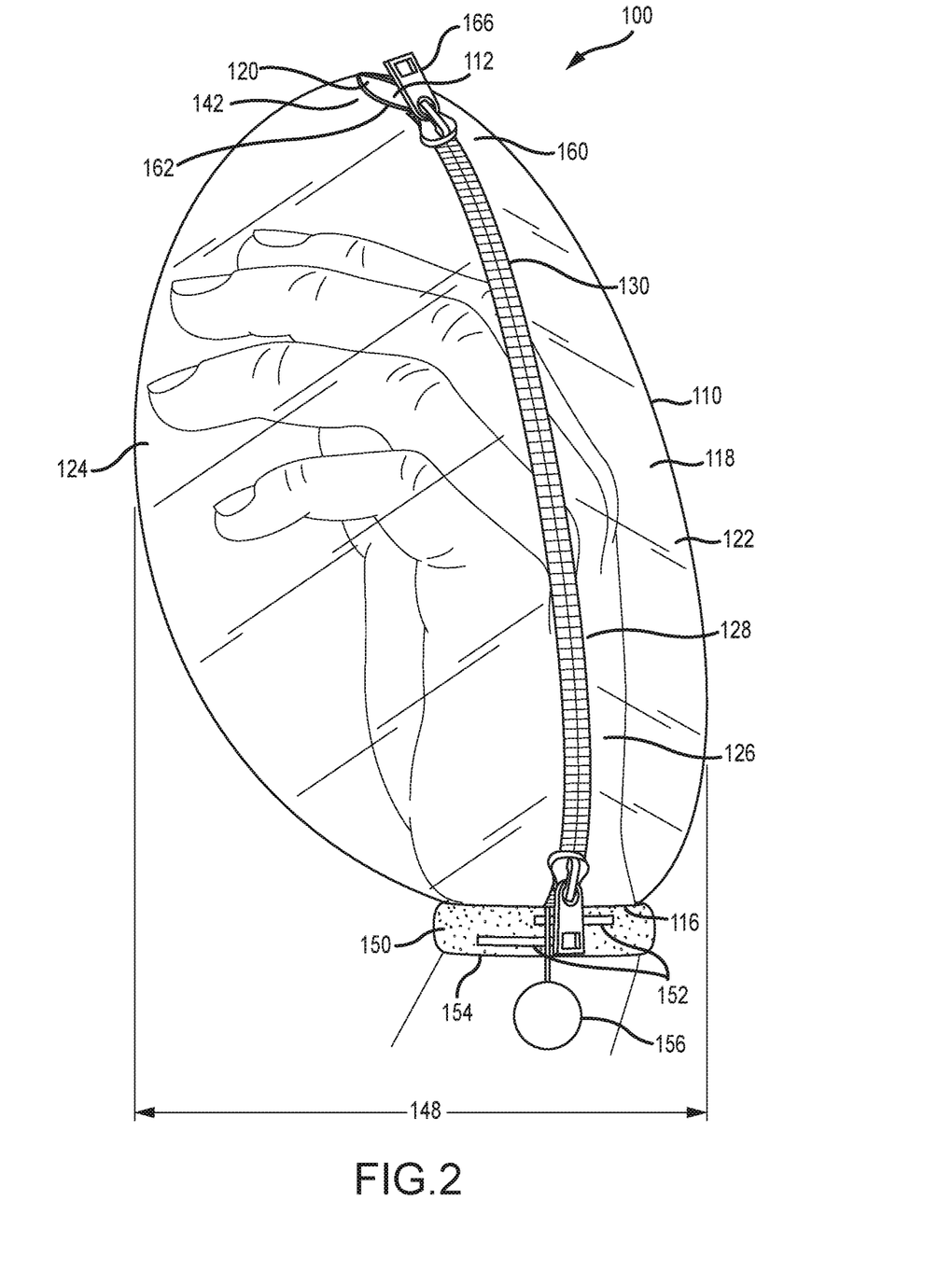
FIG. 2 is a right schematic view of the hand cover of FIG. 1 applied to a patient's hand.

FIGS. 1 and 2 depict one embodiment of a hand cover 100. A hand cover 100 may be configured for either a right hand or a left hand or both hands, with the description herein directed to the hand cover 100 used on a patient's left hand. The hand cover 100 includes a globule-shaped protective housing 110 defining an insertion aperture 154 at one end portion, and includes an adjustment mechanism 150 adjacent the insertion aperture 154. When a user's hand is received within the housing 110 through the insertion aperture 154, the adjustment mechanism 150 may secure the housing 110 to a region near or at the user's wrist or lower hand. The protective housing 110 may serve as a bubble or barrier that collectively surrounds, or substantially surrounds, the palm, fingers, and thumb of a user's hand, and inhibits the user's manipulation of items able to be reached by the hand. While the hand can cause the cover 100 to generally contact an item, the cover 100 inhibits the fine motor skills of the fingers, thumb, and palm from grasping or otherwise manipulating the item. An upper access aperture 112 may be formed in an upper portion of the protective housing 110.

The protective housing 110 may be any shape that surrounds or substantially surrounds a hand, such as an elongated or tapered spherical shape with truncated top and bottom ends as depicted in FIGS. 1-5.

The protective housing 110 may be a size that fits an adult's, a child's, or an infant's hand. When in use on a user's hand, the protective housing 110 may be tall enough that it extends to or past the user's finger tips. In embodiments, the protective housing 110 has a height 144 of from about 2 inches to about 10 inches, or from about 3 inches to about 10 inches, or from about 4 inches to about 10 inches, or from about 5 inches to about 10 inches, or from about 6 inches to about 10 inches, or from about 7 inches to about 10 inches, or from about 8 inches to about 10 inches, or from about 2 inches to about 9 inches, or from about 2 inches to about 8 inches, or from about 2 inches to about 7 inches, or from about 2 inches to about 6 inches, or from about 2 inches to about 5 inches, or from about 2 inches to about 4 inches, or from about 3 inches to about 9 inches, or from about 4 inches to about 8 inches.

When in use on a user's hand, the protective housing 110 may be wide enough that the user's fingers are not pressed together. In embodiments, the protective housing 110 has a width (diameter) 146 at the widest point of from about 3 inches to about 11 inches, or from about 4 inches to about 11 inches, or from about 5 inches to about 11 inches, or from about 6 inches to about 11 inches, or from about 7 inches to about 11 inches, or from about 8 inches to about 11 inches, or from about 9 inches to about 11 inches, or from about 3 inches to about 10 inches, or from about 3 inches to about 9 inches, or from about 3 inches to about 8 inches, or from about 3 inches to about 7 inches, or from about 3 inches to about 6 inches, or from about 3 inches to about 5 inches, or from about 4 inches to about 10 inches, or from about 5 inches to about 9 inches.

The width of the protective housing 110 at or near the upper access aperture 112 may be less than the width 146 at the widest point. In embodiments, the protective housing 110 has a width (diameter) at or near the upper access aperture 112 of from about 1 inch to about 5 inches, or from about 2 inches to about 5 inches, or from about 3 inches to about 5 inches, or from about 4 inches to about 5 inches, or from about 1 inch to about 4 inches, or from about 1 inch to about 3 inches, or from about 1 inch to about 2 inches, or from about 2 inches to about 4 inches.

The width of the protective housing 110 at or near the adjustment mechanism 150 may be less than the width 146 at the widest point. In embodiments, the protective housing 110 has a width (diameter) at or near the adjustment mechanism 150 of from about 1 inch to about 6 inches, or from about 2 inches to about 6 inches, or from about 3 inches to about 6 inches, or from about 4 inches to about 6 inches, or from about 5 inches to about 6 inches, or from about 1 inch to about 5 inches, or from about 1 inch to about 4 inches, or from about 1 inch to about 3 inches, or from about 1 inch to about 2 inches, or from about 2 inch to about 5 inches, or from about 3 inch to about 4 inches.

When in use on a user's hand, the protective housing 110 may be deep enough that the back (dorsal surface) and palm (ventral surface) of the user's hand do not touch the inner surface 120 of the protective housing 110 when the user's wrist is in a neutral position. In embodiments, the protective housing has a depth 148 of from about 0.75 inch to about 3.5 inches, or from about 1 inch to about 3.5 inches, or from about 1.25 inches to about 3.5 inches, or from about 1.5 inches to about 3.5 inches, or from about 1.75 inches to about 3.5 inches, or from about 2 inches to about 3.5 inches, or from about 0.75 inch to about 3.25 inches, or from about 0.75 inch to about 3 inches, or from about 0.75 inch to about 2.75 inches, or from about 0.75 inch to about 2.5 inches, or from about 0.75 inch to about 2.25 inches, or from about 1 inch to about 3.25 inches, or from about 1.25 inches to about 3 inches, or from about 1.5 inches to about 2.75 inches.

The protective housing 110 may be constructed of many different types of material having sufficient rigidity and shape retention to restrict or limit the use of the hand through the housing 110. For instance, the material may be generally formed of a sheet material made of plastic, such as polyethylene, polypropylene, or acrylic, man-made or natural fabric (woven or non-woven), or a combination thereof. The material may be transparent or translucent. The protective housing 110 may be constructed as a single piece or as multiple pieces. The material may be a single layer or sandwich structure of two or more layers. The protective housing may be formed by, for example, molding such as press, heat, or injection molding, or bending a sheet into a desired shape and securing the sheet in the desired shape, such as with one or more seams.

The material may be of sufficient firmness that it resists significant deformation or breakage by the weight of a user's hand or by a user's intentional effort to shape or deform the cover 100 from the inside. The material may be of sufficient strength and toughness that it resists permanent deformation or breakage upon impact with an object, such as the side rail of a hospital bed or gurney.

The protective housing 110 may have a uniform thickness or a variable thickness. A lower thickness in some areas may help reduce the weight of the hand cover 100, which may improve its comfort. A greater thickness in some areas may help increase the strength and decrease the vulnerability of the protective housing 110 in areas susceptible to impact or damage, such as cracking, breaking, or deformation. In embodiments, the protective housing 110 has a thickness of from about 0.05 mm to about 5 mm, or from about 0.5 mm to 5 mm, or from about 1 mm to 5 mm, or from about 1.5 mm to 5 mm, or from about 2 mm to 5 mm, or from about 2.5 mm to 5 mm, or from about 3 mm to 5 mm, or from about 0.5 mm to 4.5 mm, or from about 0.5 mm to 4 mm, or from about 0.5 mm to 3.5 mm, or from about 0.5 mm to 3 mm, or from about 0.5 mm to 2.5 mm, or from about 1 mm to 4.5 mm, or from about 1.5 mm to 4 mm, or from about 2 mm to 3.5 mm.

The protective housing 110 may have a uniform rigidity or stiffness or a variable stiffness. For example, a curved portion of the protective housing 110 may be stiffer than a flat portion. As another example, the protective housing 110 may be relatively more rigid in the region between the insertion aperture 154 and the upper access aperture 112, which may increase the strength of the protective housing 110 and decrease the deformability in that region. The protective housing 110 may be relatively less rigid at or near the insertion aperture 154, which may increase flexibility, increase the ability of the housing 110 to bend or flex out of the way as the hand cover 100 is applied to a hand, and increase the ease with which the hand cover 100 is applied to a hand. The protective housing 110 may be relatively less rigid at or near the upper access aperture 112, which may increase its pliability and decrease the ability of a user to use the upper access aperture 112 as a lever or pry. A relatively less rigid protective housing 110 at or near the upper access aperture 112 may also allow the aperture 112 to be openable or closable by deforming the walls 160 of the aperture 112.

The protective housing 110 of the exemplary embodiment depicted in FIGS. 1-5 includes a dorsal portion 122, a palm or ventral portion 124, an ulnar portion 126, and a thumb portion 132. By way of example but not limitation, when the hand cover 100 is not in use, the ulnar portion 126 may be identified as the portion including a lateral access aperture 128 or the thumb portion 132 may be identified as the portion including a positioning mechanism 138.

Figure 3:
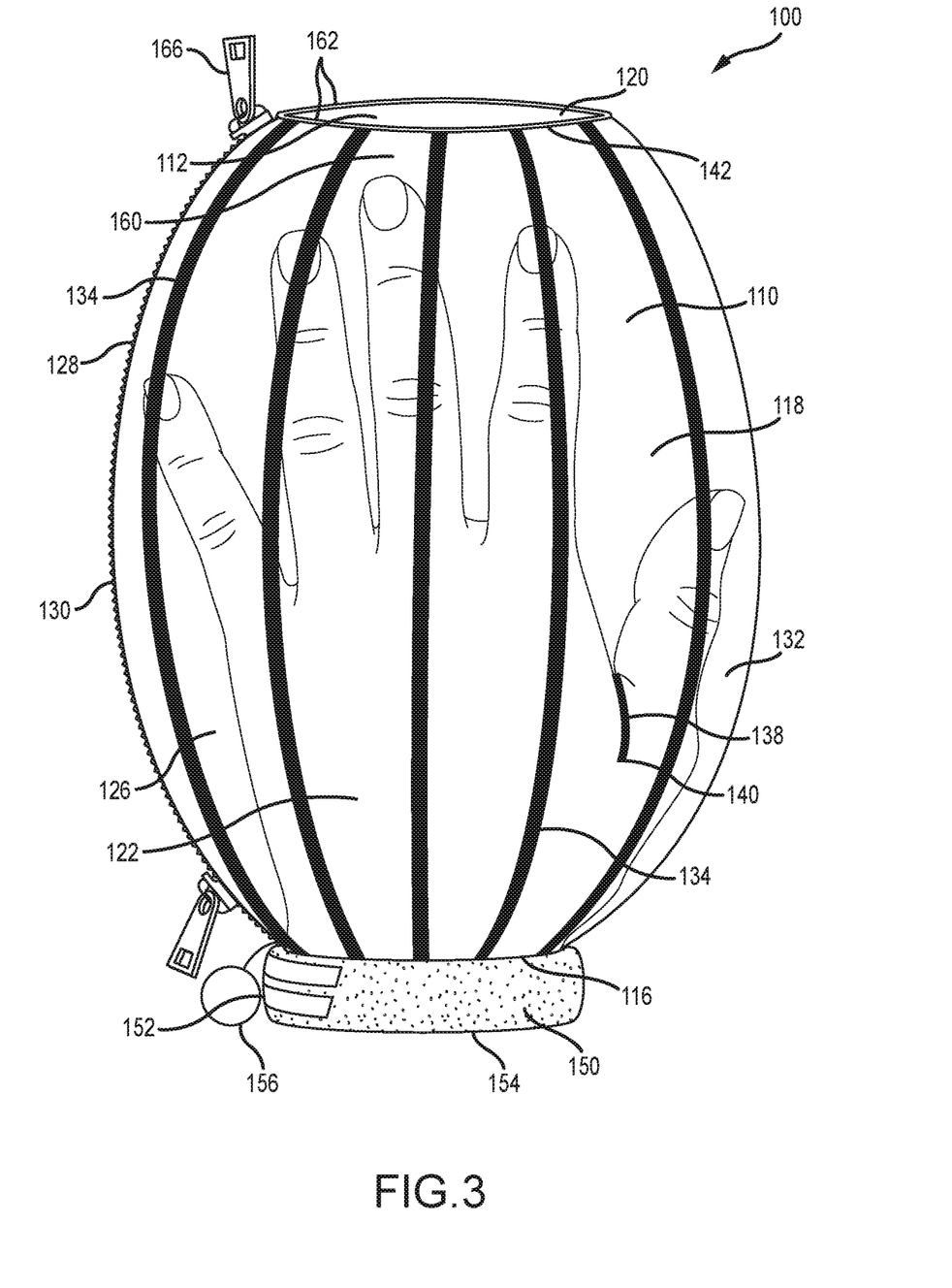
FIG. 3 is a front schematic view of a hand cover according to another embodiment applied to a patient's hand.

The outer surface 118 of the protective housing 110 may be smooth, as depicted in FIGS. 1 and 2. In some embodiments, the outer surface 118 is ribbed as depicted in FIG. 3. The ribs or struts 134 may be constructed of the same material or different material as the portions of the protective housing 110 between the ribs 134. For example, the ribs 134 may be constructed of plastic and the portions of the protective housing 110 between the ribs 134 may be constructed of fabric. The ribs 134 may provide support or strength to the protective housing 110. Each rib 134 may be oriented in any direction, such as vertically or horizontally, and all ribs 134 may be oriented in the same direction or in different directions. Each rib 134 may extend for the full distance of a given dimension such as height 144, width 146, or depth 148 of the protective housing 110, as depicted in FIG. 3, or may extend a portion of a given dimension of the protective housing 110. Ribs 134 may be positioned on any one or more of a dorsal portion 122, palm portion 124, ulnar portion 126, and thumb portion 132 of the protective housing 110.

Figure 4:
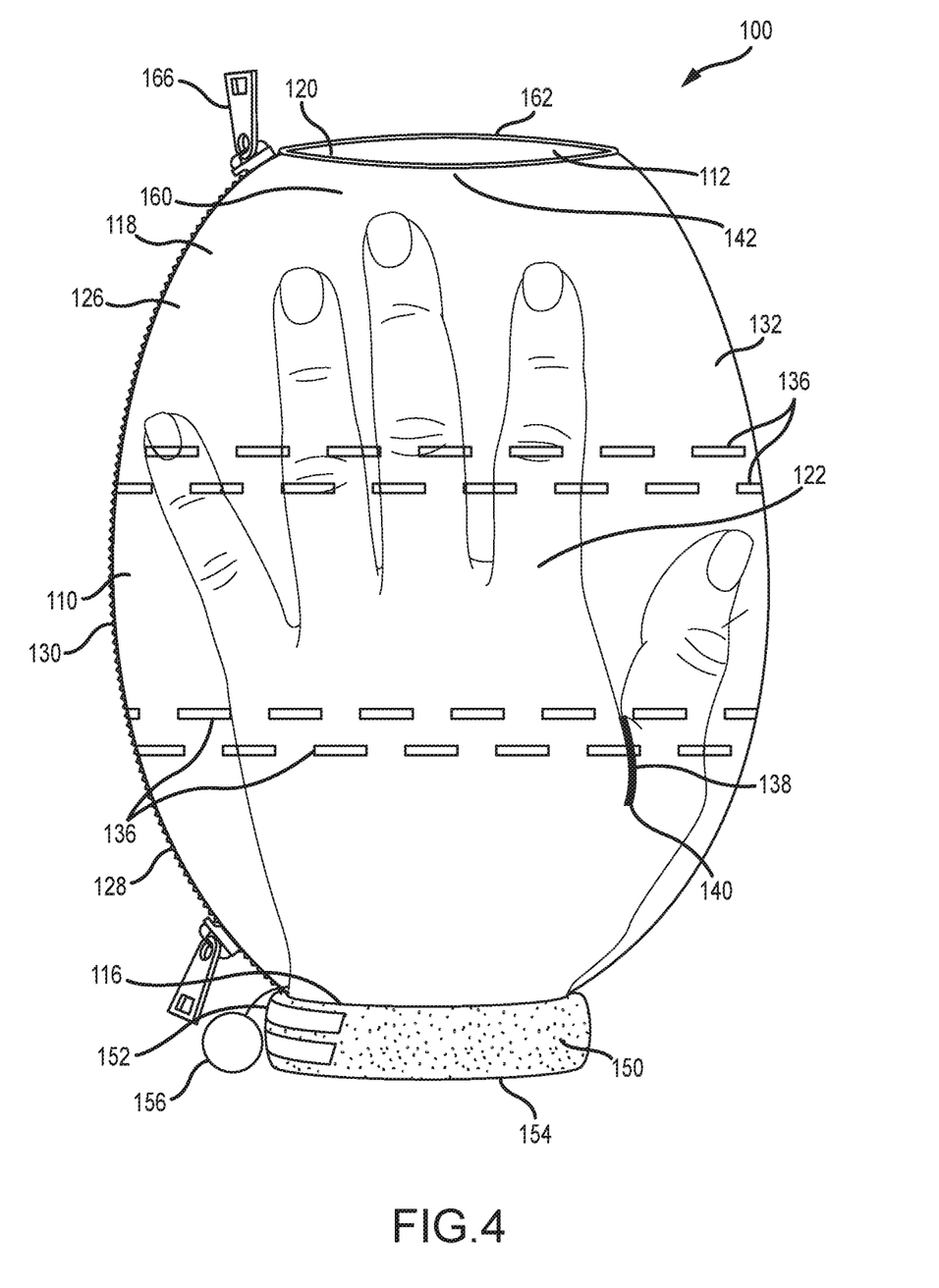
FIG. 4 is front schematic view of a hand cover according to another embodiment applied to a patient's hand.

In some embodiments, the outer surface 118 is fenestrated as depicted in FIG. 4. The fenestrae 136 may be one of many shapes, or a combination more than one shape, such as circular, triangular, square, or rectangular. The fenestrae 136 may be oriented regularly, such as in rows, or randomly. Fenestrae 136 may be positioned on any one or more of the dorsal portion 122, palm portion 124, ulnar portion 126, and thumb portion 132 of the protective housing 110.

In some embodiments, and as shown in FIGS. 1-5, the protective housing 110 includes an upper access aperture 112. The upper access aperture 112 provides air circulation and access to the upper portion of the hand, such as to apply medication to the hand or to monitor IV lines or other medical devices attached to the hand, and may help reduce a user's sense of restriction, restraint, or claustrophobia.

The upper access aperture 112 may be any shape, such as substantially circular or elliptical when open or not deformed. In embodiments, the open upper access aperture 112 has a width (diameter) of from about 1 inch to about 5 inches, or from about 2 inches to about 5 inches, or from about 3 inches to about 5 inches, or from about 4 inches to about 5 inches, or from about 1 inch to about 4 inches, or from about 1 inch to about 3 inches, or from about 1 inch to about 2 inches, or from about 2 inches to about 4 inches.

The upper access aperture 112 may be selectively openable or closable. When closed, the aperture 112 may prevent a caregiver from accessing the hand but may still permit air to enter into the hand cover 100. In some embodiments, the closed upper access aperture 112 has a width (diameter) of less than 2 inches or less than 1 inch or less than 0.5 inch. A closed upper access aperture 112 or the walls 160 surrounding a closed aperture 112 may have any shape, such as substantially circular or elliptical or a slit. An open upper access aperture 112 and a closed aperture 112 may have the same shape or a different shape. For example, when open, the aperture 112 may be substantially circular and when closed may be a substantially rectangular slit.

In some embodiments, the upper access aperture 112 is releasably closable by an upper access securing member 114, which may be one of many types of fastener. Fasteners may include, for example, zippers, buttons, snaps, hook-and-loop fasteners, or hook-and-eye fasteners. For example, engaging a complimentary hook-securing member 114 and loop-securing member 114 may close the upper access aperture 112. In some embodiments, the upper access aperture 112 is releasably closable by a flap or cap that may be positioned across the upper access aperture 112 when the flap or cap is in the closed position and may be withdrawn from the upper access aperture 112 when the flap or cap is in the open position. In some embodiments, the upper access aperture 112 is mechanically releasably openable. By deforming the protective housing 110, such as by pressing on the sides 142 of the upper access aperture 112, the walls 160 surrounding the upper access aperture 112 are deformed and cause the aperture 112 to open. Eliminating the external forces causing the deformation of the walls 160 allows the housing walls 160 and upper access aperture 112 to return to the closed position.

In some embodiments, the edges 162 of the walls 160 surrounding the upper access aperture 112 are rounded or curved, which may decrease the ability of a user to use an edge 162 as a lever or pry. In some embodiments, the edges 162 are relatively less rigid than other portions of the protective housing 110, which may increase their pliability and decrease their functionality as levers or pries.

In the exemplary embodiments depicted in FIGS. 1-5, the protective housing 110 includes a lateral access aperture 128. The lateral access aperture 128 may provide access to the hand while the hand cover 100 is in use and without needing to remove the hand cover 100. In some embodiments, the lateral access aperture 128 extends along the entire length of the protective housing 110, as shown in FIG. 2, which helps maximize access to the hand for, for example, caring for wounds; inserting, monitoring, or removing IV lines or other medical devices; adjusting a positioning mechanism 138; or adjusting a cocking mechanism 176. In some embodiments, the lateral access aperture 128 extends along a portion of the length of the protective housing 110, which may decrease the accessibility of the hand compared to an aperture 128 that extends along the entire length of the housing 110. The lateral access aperture 128 may be releasably closable by a lateral securing mechanism 130, which may be any one of many fasteners. Fasteners may include, for example, zippers, buttons, snaps, hook-and-loop fasteners, or hook-and-eye fasteners. In the exemplary embodiments depicted in FIGS. 1-5, the lateral access aperture 128 may be a zipper, which may include one or more pull tabs 166 for opening or closing the zipper. With reference to FIG. 2, the lateral access aperture 128 may be positioned on the ulnar portion 126 of the protective housing 110, which permits the user to naturally move his or her hands towards the face or chest without the lateral securing mechanism 130 scratching or otherwise irritating the face or chest. Positioning the lateral access aperture 128 on the ulnar portion 126 also permits a caregiver to conveniently access the aperture 128 and hand.

In the exemplary embodiments depicted in FIGS. 1-5, the protective housing 110 includes a positioning mechanism 138, which may be a strap, loop, hook, or other securing device. The positioning mechanism 138 may help maintain the hand cover 100 in place on a user's hand, such as by capturing the user's thumb and inhibiting the hand cover 100 from rotating around the user's hand and inhibiting the user's hand from sliding to or through the upper access aperture 112. When present, the positioning mechanism is located near the thumb portion 132 of the protective housing 110. When in use, and as depicted in FIGS. 1-5, the positioning mechanism 138 may be positioned over the base of the user's thumb. The positioning mechanism 138 may be constructed of a soft flexible material such as fabric, ribbon, or cord, or may be constructed of a stiff material such as plastic. The length of the positioning mechanism 138 may be adjustable. The positioning mechanism 138 may be secured to the inner surface 120 of the protective housing 110 at one or more positioning mechanism attachment sites 140. The positioning mechanism 138 may be secured by stitches, glue, staples, tape, bonding, fasteners, or any combination thereof. In one embodiment, the positioning mechanism 138 is releasably secured at at least one attachment site 140, which enables adjusting the length of the mechanism 138 and thereby helps customize the fit of the mechanism 138 to a user. In one embodiment, the positioning mechanism 138 includes a series of two or more button holes than run along the length of the mechanism 138 from a fixed end that is permanently attached to an attachment site 140 towards a free end capable of being secured to a second attachment site 140 that is a button. The positioning mechanism 138 may be secured to the protective housing 110 by buttoning the button-attachment site 140 to the button hole closest to the free end of the mechanism 138. Securing the positioning mechanism 138 to the protective housing 110 at a button hole closer to the fixed end decreases the length of the mechanism 138 and maintains it at its decreased length.

As shown in FIGS. 1-5, the protective housing 110 is secured to a user's arm at or near the wrist by the adjustment mechanism 150 attached to the protective housing 110 adjacent the insertion aperture 154. In the exemplary embodiment, the protective housing 110 is secured to the adjustment mechanism 150 at a juncture 116. A juncture 116 may be formed by any known means including, but not limited to, stitches, glue, tape, bonding, or any combination thereof. The adjustment mechanism 150 may be secured along the entire juncture 116 or a portion of the juncture 116. The adjustment mechanism 150 may help maintain the protective housing 110 in place while the hand cover 100 is in use, such as by inhibiting the hand cover 100 from being withdrawn over the user's hand or pushed down the user's forearm. The adjustment mechanism 150 may be constructed of any soft material such as fabric, foam, padding, gel-filled pouch, or combinations thereof. The fabric material may be any natural or synthetic fabric such as cotton, elastane or spandex, microfiber, polyester, rayon, silk, viscose, or wool, or any combination thereof. The material may be stretchable, which may help secure the adjustment mechanism 150 to the user's wrist and may also provide versatile adjustability of the circumference of the adjustment mechanism 150. The adjustment mechanism 150 may be constructed as a single piece or as multiple pieces.

The adjustment mechanism 150 may be sufficiently long such that it is capable of encircling the wrist of a user. The size or circumference of the adjustment mechanism 150 may be adjustable to help provide a tighter or looser fit of the adjustment mechanism 150 around the user's wrist. The size of the adjustment mechanism 150 may be adjusted and secured at its adjusted size by at least one adjustment member 152, which may be a drawstring, strap, hook-and-loop closure, hook-and-eye closure, snap, button, or any combination thereof. For example, when the adjustment member 152 is a hook-and-loop closure (Velcro), the adjustment member 152 can be pulled to tighten the fit of the adjustment mechanism 150, such as by decreasing the effective circumference of the adjustment mechanism 150. The Velcro-adjustment member 152 can be releasably secured to the adjustment mechanism 150 by pressing it against a complimentary Velcro-adjustment member 152 positioned on the adjustment mechanism 150. Securing the Velcro-adjustment member 152 helps maintain the adjusted size of the adjustment mechanism 150 until the Velcro-adjustment members 152 are released. Separating the complimentary Velcro-adjustment members 152 loosens the fit of the adjustment mechanism 150 by increasing the effective circumference of the adjustment mechanism 150. The adjustment member 152 helps fit the adjustment mechanism 150 to all sizes of users' wrists.

In some embodiments, the full or unadjusted circumference of the adjustment mechanism 150 is from about 2 inches to about 10 inches, or from about 3 inches to about 10 inches, or from about 4 inches to about 10 inches, or from about 5 inches to about 10 inches, or from about 6 inches to about 10 inches, or from about 7 inches to about 10 inches, or from about 8 inches to about 10 inches, or from about 2 inches to about 9 inches, or from about 2 inches to about 8 inches, or from about 2 inches to about 7 inches, or from about 2 inches to about 6 inches, or from about 2 inches to about 5 inches, or from about 2 inches to about 4 inches, or from about 3 inches to about 9 inches, or from about 4 inches to about 8 inches, or from about 5 inches to about 7 inches. In some embodiments, adjusting the adjustment mechanism 150 may decrease the circumference by about 10% to about 50%, or by about 15% to about 50%, or by 20% to about 50%, or by 25% to about 50%, or by 30% to about 50%, or by 35% to about 50%, or by about 10% to about 45%, or by about 10% to about 40%, or by about 10% to about 35%, or by about 10% to about 30%, or by about 10% to about 25%, or by about 15% to about 45%, or by about 20% to about 40%, or by about 25% to about 35%.

The adjustment mechanism 150 is functionally attached to the protective housing 110 adjacent the insertion aperture 154. The insertion aperture 154 may be substantially circular in shape and may be large enough that a user's hand can be inserted through the aperture 154. In some embodiments, the circumference of the insertion aperture 154 is from about 2 inches to about 10 inches, or from about 3 inches to about 10 inches, or from about 4 inches to about 10 inches, or from about 5 inches to about 10 inches, or from about 6 inches to about 10 inches, or from about 7 inches to about 10 inches, or from about 8 inches to about 10 inches, or from about 2 inches to about 9 inches, or from about 2 inches to about 8 inches, or from about 2 inches to about 7 inches, or from about 2 inches to about 6 inches, or from about 2 inches to about 5 inches, or from about 2 inches to about 4 inches, or from about 3 inches to about 9 inches, or from about 4 inches to about 8 inches, or from about 5 inches to about 7 inches.

In some embodiments, and as shown in FIGS. 1-4, the adjustment mechanism 150 includes an attachment anchor 156. The attachment anchor 156 may be configured to have devices such as restraints, cords, or bands attached to it. For example, elasticized exercise bands may be attached to an attachment anchor 156. The attachment anchor 156 may be a ring, loop, hook, tab, or similar structure. In some embodiments, the attachment anchor 156 is positioned on the adjustment mechanism 150 near or in line with the ulnar portion 126 of the protective housing 110, which permits the user to naturally move his or her hands towards the face or chest without the attachment anchor 156 wounding or irritating the face or chest. Positioning the attachment anchor 156 near or in line with the ulnar portion 126 also permits a caregiver to conveniently access the anchor 156 and hand.

With reference to FIG. 1, in some embodiments, the adjustment mechanism 150 includes at least one retention device 158, which may be a strap, such as a Velcro strap, loop, or other securing device. The retention device 158 may be secured to the adjustment mechanism 150 by stitches, glue, staples, tape, bonding, fasteners, or any combination thereof. The retention device 158 may help secure devices such as cords, tubes, or IV lines in a desired position, such as away from the user's hand. For example, when the retention device 158 is a strap, an IV line may be captured between the retention device 158 and the adjustment mechanism 150 such that the IV line can be selectively positioned. Securing an IV line or other device to the adjustment mechanism 150 also helps to avoid placing medical tape on a user's skin, which can irritate or abrade the skin upon removal.

Figure 5:
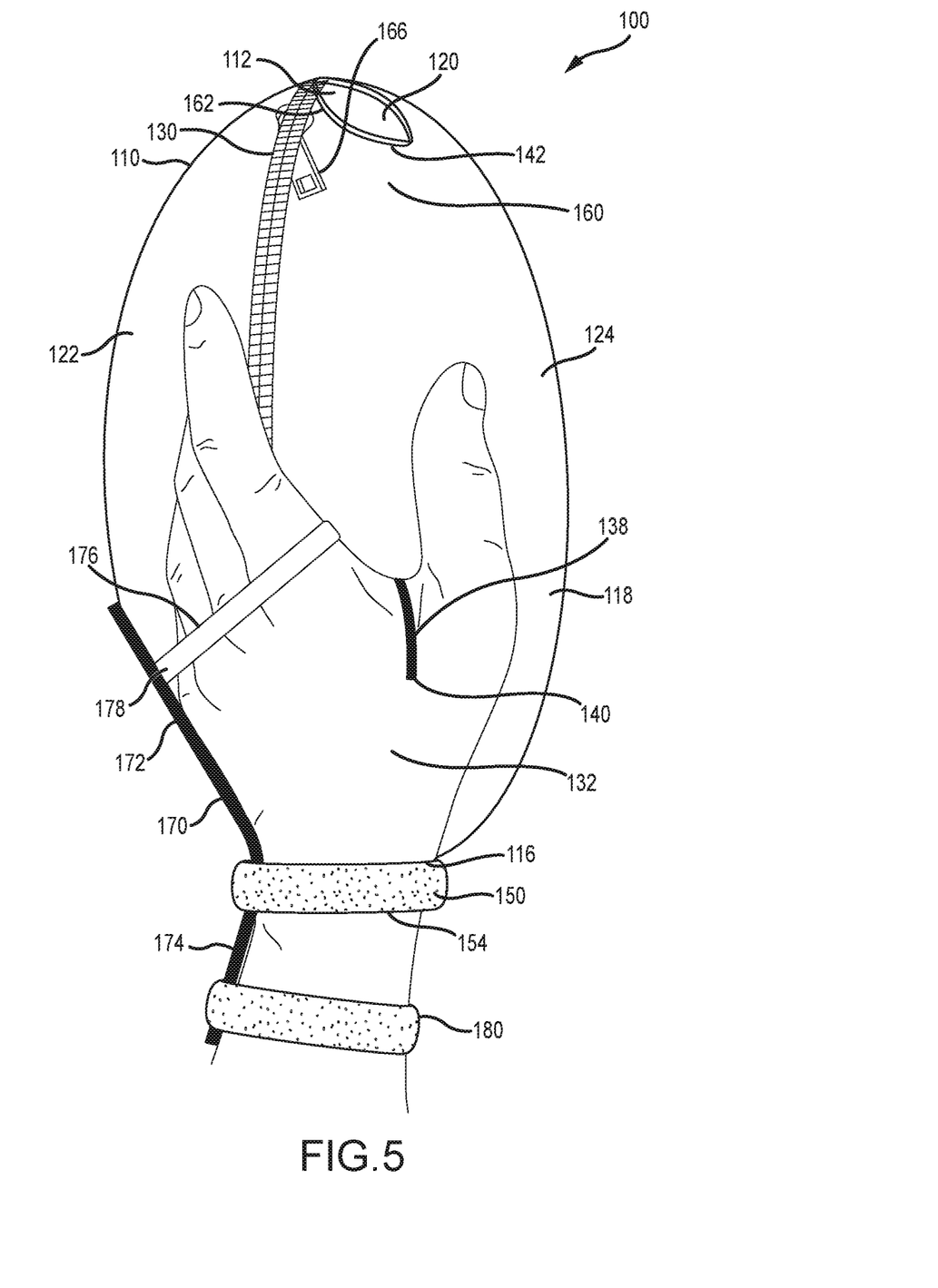
FIG. 5 is a right schematic view of a hand cover according to another embodiment applied to a patient's hand.

In some embodiments, and as depicted in FIG. 5, the hand cover 100 includes a splint 170. The splint 170 may help maintain the hand or wrist in a cocked position, such as when an arterial IV line has been inserted in or near the wrist. The splint 170 may be constructed of any rigid and lightweight material. The material may be plastic, such as polyethylene, polypropylene, or acrylic. The material may be of sufficient stiffness that it supports the wrist and hand in a cocked position. The material may be the same as or different from the material of the protective housing 110. The splint 170 may be constructed as a single piece or as multiple pieces. The protective housing 110 with the splint 170 may be constructed as a single piece or as multiple pieces.

The splint 170 may be generally L-shaped when viewed in profile (see FIG. 5). The splint 170 may include a hand portion 172 and a wrist portion 174. The hand portion 172 may be integrated into or separate from but positioned adjacent to the protective housing 110. The hand portion 172 may be substantially rectangular in shape when viewed in rear plan view. The width of the hand portion 172 may be approximately the width of the dorsal portion 122 of the protective housing 110 or approximately the width of a hand. The hand portion 172 may extend from the fingers to the wrist. In the exemplary embodiment depicted in FIG. 5, the hand portion 172 extends from at or near the proximal phalanges to the wrist. In embodiments, the length of the hand portion is from about 1 inch to about 5 inches, or from about 1.5 inches to about 5 inches, or from about 2 inches to about 5 inches, or from about 2.5 inches to about 5 inches, or from about 3 inches to about 5 inches, or from about 1 inch to about 4.5 inches, or from about 1 inch to about 4 inches, or from about 1 inch to about 3.5 inches, or from about 1 inch to about 3 inches, or from about 1.5 inches to about 4.5 inches, or from about 2 inches to about 4 inches.

The hand portion 172 may join the wrist portion 174 at or near the adjustment mechanism 150. The splint 170 may bend at approximately 10° to 60° away from the plane of the hand portion 172 at or near the adjustment mechanism 150. The hand portion 172 may be integrated into or separate from but positioned adjacent to the adjustment mechanism 150. The wrist portion 174 may be an extension of or separate from the protective housing 110.

In the exemplary embodiment depicted in FIG. 5, the wrist portion 174 extends from the wrist beyond the insertion aperture 154 and down the forearm. The wrist portion 174 may be substantially rectangular in shape when viewed in rear plan view.

The width of the wrist portion 174 may be approximately the width of the hand portion 172 or approximately the width of a wrist. In embodiments, the wrist portion 174 has a width of from about 1 inch to about 4 inches, or from about 1.5 inches to about 4 inches, or from about 2 inches to about 4 inches, or from about 2.5 inches to about 4 inches, or from about 1 inch to about 3.5 inches, or from about 1 inch to about 3 inches, or from about 1 inch to about 2.5 inches, or from about 1.5 inches to about 3.5 inches, or from about 2 inches to about 3 inches.

A cocking mechanism 176, which may be a strap, bar, loop, or other securing device, may help maintain the hand or wrist in a cocked position, such as by capturing the user's hand and inhibiting the hand from moving towards the neutral position. The cocking mechanism 176 may be constructed of a stiff material such as plastic. The material may be of sufficient stiffness that it resists the force of the hand naturally or intentionally moving away from the cocked position. The cocking mechanism 176 may be constructed of a soft flexible material such as elastic, fabric, ribbon, or cord. The material may have sufficient resistance that it resists the force of the hand naturally or intentionally moving away from the cocked position. When in use, and as depicted in FIG. 5, the cocking mechanism 176 may be positioned around and across the user's fingers or palm such that the user's fingers are or palm is captured between the cocking mechanism 176 and the hand portion 172 of the splint 170.

The cocking mechanism 176 may be permanently or releasably attached to the inner surface 120 of the dorsal portion 122 of the protective housing 110 at one or more cocking mechanism attachment sites 178. Releasably securing the cocking mechanism 176 enables adjustment of the length of the mechanism 176 and thereby helps customize the fit of the mechanism 176 to a user. The cocking mechanism 176 may be secured by stitches, glue, staples, tape, bonding, fasteners, or any combination thereof. In one embodiment, the cocking mechanism 176 includes a series of two or more button holes that run along the length of the mechanism 176 from a fixed end that is permanently attached to an attachment site 164 towards a free end capable of being secured to a second attachment site 164 that is a button. The cocking mechanism 176 may be secured to the protective housing 110 by buttoning the button-attachment site 164 to the button hole closest to the free end of the mechanism 176. Securing the cocking mechanism 176 to the protective housing 110 at a button hole closer to the fixed end decreases the length of the mechanism 176 and maintains it at its decreased length.

With continued reference to FIG. 5, an optional splint securing mechanism 180 may help maintain the splint 170 in place while the hand cover 100 is in use. The splint securing mechanism 180 may be constructed of any soft material such as fabric, foam, padding, gel-filled pouch, or combinations thereof. The fabric material may be any natural or synthetic fabric such as cotton, elastane or spandex, microfiber, polyester, rayon, silk, viscose, wool, or any combination thereof. The material may be stretchable, which may help secure the splint securing mechanism 180 to the user's forearm and may also provide versatile adjustability of the circumference of the splint securing mechanism 180. The material may be the same as or different from the material of the adjustment mechanism 150. The splint securing mechanism 180 may be constructed as a single piece or as multiple pieces.

The splint securing mechanism 180 may be substantially circular in shape such that it is capable of encircling the forearm of a user. The size or circumference of the splint securing mechanism 180 may be adjustable to help provide a tighter or looser fit of the splint securing mechanism 180 around the user's forearm. The size of the splint securing mechanism 180 may be adjusted and secured at its adjusted size by at least one splint adjustment member (not shown), which may be a drawstring, strap, hook-and-loop closure, hook-and-eye closure, snap, button, or any combination thereof. The split adjustment member helps fit the splint securing mechanism 180 to all sizes of users' wrists.

In some embodiments, the full or unadjusted circumference of the splint securing mechanism 180 is from about 2 inches to about 12 inches, or from about 3 inches to about 12 inches, or from about 4 inches to about 12 inches, or from about 5 inches to about 12 inches, or from about 6 inches to about 12 inches, or from about 7 inches to about 12 inches, or from about 8 inches to about 12 inches, or from about 9 inches to about 12 inches, or from about 2 inches to about 11 inches, or from about 2 inches to about 10 inches, or from about 2 inches to about 9 inches, or from about 2 inches to about 8 inches, or from about 2 inches to about 7 inches, or from about 2 inches to about 6 inches, or from about 2 inches to about 5 inches, or from about 2 inches to about 4 inches, or from about 3 inches to about 11 inches, or from about 4 inches to about 10 inches, or from about 5 inches to about 9 inches, or from about 6 inches to about 8 inches. In some embodiments, adjusting the splint securing mechanism 180 may decrease the circumference by about 10% to about 50%, or by about 15% to about 50%, or by 20% to about 50%, or by 25% to about 50%, or by 30% to about 50%, or by 35% to about 50%, or by about 10% to about 45%, or by about 10% to about 40%, or by about 10% to about 35%, or by about 10% to about 30%, or by about 10% to about 25%, or by about 15% to about 45%, or by about 20% to about 40%, or by about 25% to about 35%.

Methods of Use of the Hand Cover

By way of example, but not limitation, the hand cover 100 of FIGS. 1-4 may be used to inhibit a user from moving or removing medical interventions according to the following procedure. While the adjustment mechanism 150 is loose or not tightened, such that the effective circumference of the adjustment mechanism 150 is relatively large, the hand cover 100 may be guided over a user's (patient's) hand such that the fingertips pass through the insertion aperture 154 and in to the protective housing 110 until the adjustment mechanism 150 encircles the wrist. The hand cover 100 can be slid over the hand with minimal contact with the hand, which minimizes disturbance to and stress on the user.

The adjustment mechanism 150 is secured to the wrist by tightening the adjustment member 152. A drawstring-adjustment member 152 is tightened by pulling on the drawstring and is secured in its tightened position by tying or knotting the drawstring close to the adjustment mechanism 150 or by sliding a cord lock to be adjacent to the adjustment mechanism 150.

The hand cover 100 of the embodiments depicted in FIGS. 1-5 may include an upper access aperture 112. By way of example, but not limitation, a hand cover 100 may be used with an upper access aperture 112 to inhibit a user from moving or removing medical interventions as well as to provide air circulation and access to the hand and reduce a user's sense of restriction, restraint, or claustrophobia according to the following procedure.

The hand cover 100 may be applied to a user's hand according to the method described above. The hand cover 100 is guided over a user's hand until the fingertips are at or near the upper access aperture 112. The upper access aperture 112 may be open or closed when the hand cover 100 is guided over the hand. At any time during use, the upper access aperture 112 may be opened or closed. For example, the upper access aperture 112 may be closed by engaging the upper securing access members 114 and opened by releasing the upper access securing members 114. As another example, the upper access aperture 112 may be opened by pressing on the sides 142 of the aperture 112 and closed by releasing pressure on the sides 142.

The hand cover 100 of the embodiments depicted in FIGS. 1-5 may include a positioning mechanism 138. By way of example, but not limitation, a hand cover 100 may be used with a positioning mechanism 138 to inhibit a user from moving or removing medical interventions as well as to maintain the hand cover 100 in place according to the following procedure.

The hand cover 100 may be applied to a user's hand according to any method described above. The hand cover 100 is guided over the user's hand such that the positioning mechanism 138 is positioned across the base of the thumb. The thumb is positioned between the positioning mechanism 138 and the inner surface 120 of the thumb portion 132 of the protective housing 110. The remaining fingers are positioned between the positioning mechanism 138 and the inner surface 120 of the ulnar portion 126 of the protective housing 110. The positioning mechanism 138 may be adjusted and secured by pulling on a free end of the mechanism 138 and fastening a button hole on the mechanism 138 to a button-attachment site 140 on the inner surface 120 of the protective housing 110.

The hand cover 100 of the embodiments depicted in FIGS. 1-5 may include a lateral access aperture 128. By way of example, but not limitation, a hand cover 100 may be used with a lateral access aperture 128 to inhibit a user from moving or removing medical interventions as well as to provide access to the hand without removing the hand cover 100 according to the following procedure.

The hand cover 100 may be applied to a user's hand according to any method described above. The lateral access aperture 128 is positioned alongside or near the little (most ulnar) finger. The lateral access aperture 128 may be open or closed when the hand cover 100 is guided over the hand. When the lateral access aperture 128 is open while the hand cover 100 is being applied, the hand and a positioning mechanism 138 may be accessible such that the positioning mechanism 138 can be guided into position over the base of the thumb. At any time during use, the lateral access aperture 128 may be opened or closed. For example, the lateral access aperture 128 may be closed by zipping up a zipper-lateral securing mechanism 130 and opened by unzipping a zipper-lateral securing mechanism 130.

The hand cover 100 of the embodiments depicted in FIGS. 1-5 may include an attachment anchor 156. By way of example, but not limitation, a hand cover 100 may be used with an attachment anchor 156 to inhibit a user from moving or removing medical interventions as well as to restrain a user or allow a user to perform therapeutic exercises according to the following procedure.

The hand cover 100 may be applied to a user's hand according to any method described above. The attachment anchor 156 is positioned on the ulnar side of the wrist. A device such as a restraint, exercise band, or strengthening cord is secured to the attachment anchor 156 such as by threading one end of the device through a ring-attachment anchor 156 and tying or knotting the device to secure it to the attachment anchor 156. The other end of the device may be tied to the user's bedframe. A restraint may be used for a patient who is violent or who exhibits spastic movements. A strengthening cord or exercise band may be used to provide resistance such that a user can perform muscle strengthening or toning exercises or other therapeutic upper extremity movements while still in the critical care setting.

The hand cover 100 of the embodiments depicted in FIGS. 1-5 may include a retention device 158. By way of example, but not limitation, a hand cover 100 may be used with a retention device 158 to inhibit a user from moving or removing medical interventions as well as to secure devices in a desired location according to the following procedure.

The hand cover 100 may be applied to a user's hand according to any method described above. The retention device 158 is positioned at or near the dorsal surface of the wrist. An arterial IV line placed in the wrist may be positioned toward a desired location, such as away from the hand, and secured between a strap-retention device 158 and the adjustment mechanism 150. Securing an IV line or other device to the adjustment mechanism 150 with a retention device 158 also helps to avoid placing medical tape on a user's skin, which can irritate or abrade the skin upon removal.

The hand cover 100 of the embodiment depicted in FIG. 5 may include a splint 170 and cocking mechanism 176. By way of example, but not limitation, a hand cover 100 may be used with a splint 170 and cocking mechanism 176 to inhibit a user from moving or removing medical interventions as well as to maintain the hand or wrist in a cocked position according to the following procedure.

The hand cover 100 may be applied to a user's hand according to any method described above. In embodiments wherein the cocking mechanism 176 is permanently attached to the protective housing 110, the hand cover 100 may be guided over the user's hand such that the cocking mechanism 176 is positioned around the fingers or the palm of the hand. In embodiments wherein the cocking mechanism 176 is releasably attached to the protective housing 110, the cocking mechanism 176 may be secured snugly around the fingers or palm of the hand after the hand cover 100 is in position. The palm is or fingers are positioned between the cocking mechanism 176 and the inner surface 120 of the dorsal portion 122 of the protective housing 110.

When provided, the splint securing mechanism 180 is tightened, such as by pulling on a drawstring, around the forearm to help maintain the splint 170 in place.

All directional references (e.g., dorsal, ventral, proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples, and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A hand cover comprising:
an approximately globule-shaped protective housing member configured to encircle the entirety of a user's hand and constructed of a firm plastic layer to resist deformation;
an insertion aperture adapted to receive the user's hand;
an upper access aperture adapted to provide access to the user's hand, wherein the protective housing member is relatively less rigid in a first region near the insertion aperture than in a second region between the first region and the upper access aperture, to decrease deformability of the protective housing member in the second region relative to the first region; and
an adjustment mechanism including
at least one adjustment member configured to adjust a circumference of the adjustment mechanism.

2. The hand cover of claim 1, wherein the protective housing member is ribbed or fenestrated.

3. The hand cover of claim 1, wherein the upper access aperture is releasably closable.

4. The hand cover of claim 3, wherein the protective housing member includes walls surrounding the upper access aperture, and pressing on the walls deforms the walls causing the upper access aperture to open.

5. The hand cover of claim 4, wherein releasing the walls allows the upper access aperture to return to a closed position.

6. The hand cover of claim 1, wherein the protective housing member further comprises a releasably closable lateral access aperture.

7. The hand cover of claim 6, wherein the lateral access aperture is releasably closable by a zipper.

8. The hand cover of claim 1, wherein the protective housing member further comprises a positioning mechanism affixed to the interior of the protective housing member.

9. The hand cover of claim 1, wherein the adjustment mechanism further comprises an attachment anchor configured to receive at least one restraint or exercise band.

10. The hand cover of claim 1, further comprising a splint and a cocking mechanism.

11. The hand cover of claim 10, wherein the splint comprises a hand portion and a wrist portion.

12. The hand cover of claim 1, wherein a width of the upper access aperture is less than a widest width of the protective housing member.

13. The hand cover of claim 1, wherein the decreased deformability of the protective housing member in the region maintains the upper access aperture in an open shape.

14. The method of claim 1, wherein the upper access aperture is releasably closable and a width of the upper access aperture is less than a widest width of the protective housing member.

15. A method of inhibiting a patient from moving or removing a medical intervention comprising
applying a hand cover to a hand of the patient, wherein the hand cover comprises
an approximately globule-shaped protective housing member configured to encircle the entirety of the patient's hand and constructed of a firm plastic layer to resist deformation;
an insertion aperture adapted to receive the patient's hand;
an upper access aperture adapted to provide access to the patient's hand, wherein the protective housing member is relatively less rigid in a first region near the insertion aperture than in a second region between the first region and the upper access aperture, to decrease deformability of the protective housing member in the second region relative to the first region; and
an adjustment mechanism including at least one adjustment member capable of adjusting a circumference of the adjustment mechanism; and
securing the adjustment mechanism to the wrist of the patient by decreasing the circumference of the adjustment member, thereby inhibiting the patient from moving or removing a medical intervention.

16. The method of claim 15, wherein the protective housing member extends at least to the patient's finger tips.

17. The method of claim 15, wherein the upper access aperture is configured to allow air circulation to the hand.

18. The method of claim 15, wherein the protective housing member further comprises a releasably closable lateral access aperture.

19. The method of claim 15, wherein the protective housing member further comprises a positioning mechanism and the positioning mechanism is positioned across a base of a thumb.

20. A hand cover comprising:
an approximately globule-shaped protective housing member configured to encircle the entirety of a user's hand and constructed of a firm plastic layer to resist deformation;
an insertion aperture adapted to receive the user's hand;
an upper access aperture adapted to provide access to the user's hand, wherein the protective housing member is relatively more rigid in a first region near the insertion aperture than in a second region between the first region and the upper access aperture, to increase deformability of the protective housing member in the second region relative to the first region; and
an adjustment mechanism including at least one adjustment member configured to adjust a circumference of the adjustment mechanism.

\* \* \* \* \*